United States Patent [19]

Wall et al.

[11] 4,139,556
[45] Feb. 13, 1979

[54] MONO-OL FROM DIOL AND IMPROVED CITRIC ACID PROCESS

[75] Inventors: Robert G. Wall, Pinole; Shigeto Suzuki, San Francisco, both of Calif.

[73] Assignee: Chevron Research Company, San Francisco, Calif.

[21] Appl. No.: 841,170

[22] Filed: Oct. 11, 1977

Related U.S. Application Data

[60] Division of Ser. No. 681,678, Apr. 29, 1976, Pat. No. 4,079,088, which is a continuation-in-part of Ser. No. 535,457, Dec. 23, 1974, abandoned.

[51] Int. Cl.$^2$ ............................................. C07C 59/16
[52] U.S. Cl. ................................................... 562/540
[58] Field of Search ......................... 260/535 P, 642 R

[56] References Cited

U.S. PATENT DOCUMENTS

| 3,799,980 | 3/1974 | Kiyoshi et al. | 260/535 P |
| 4,022,823 | 5/1977 | Wilkes et al. | 260/535 |

*Primary Examiner*—Paul J. Killos
*Attorney, Agent, or Firm*—D. A. Newell; John Stoner, Jr.; A. T. Bertolli

[57] ABSTRACT

A process for producing 3-methyl-3-buten-1-ol from 3-methyl-2-pentene-1,5-diol which comprises heating 3-methyl-2-pentene-1,5-diol at a temperature between 200° and 450° C. in the presence of isobutene.

According to a preferred embodiment, the heating step and a distillation step to separate 3-methyl-2-pentene-1,5-diol from 3-methylene-1,5-pentanediol is incorporated into a citric acid synthesis method to increase the yield of citric acid from isobutene plus formaldehyde.

3 Claims, 1 Drawing Figure

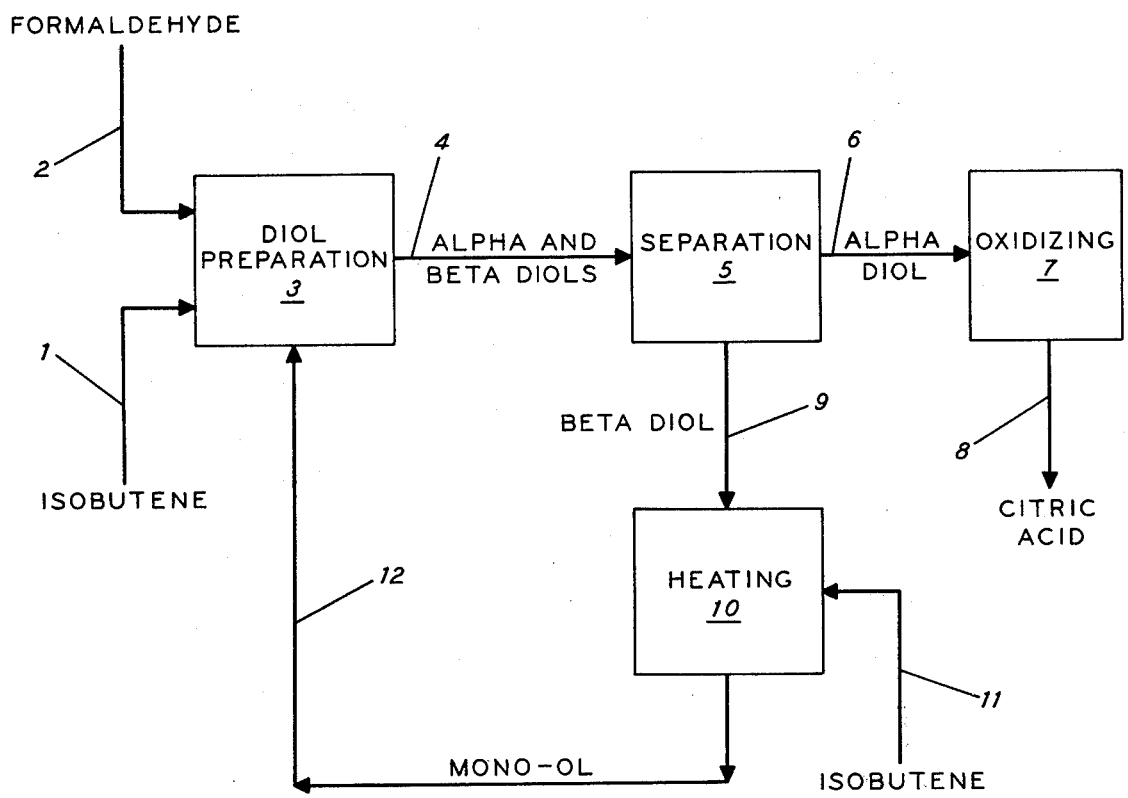

MONO-OL FROM DIOL AND IMPROVED CITRIC ACID PROCESS

CROSS-REFERENCE TO RELATED APPLICATION

This is a division of application Ser. No. 681,678, filed Apr. 29, 1976, now U.S. Pat. No. 4,079,088, which is a continuation-in-part of U.S. application Ser. No. 535,457, filed Dec. 23, 1974, now abandoned.

BACKGROUND OF THE INVENTION

The present invention relates to the production of an alkene mono-ol and also to the synthesis of citric acid.

Production of alkene mono-ols is disclosed in U.S. Pat. No. 3,574,773. Thus, according to Example 4 of U.S. Pat. No. 3,574,773, formaldehyde is reacted with isobutene to obtain mono-ol.

U.S. Pat. No. 3,692,848 discloses the production of alkenediols from mono-ol by reaction of the mono-ol with formaldehyde.

Commonly assigned patent applications Ser. Nos. 379,511 and 427,176 disclose the preparation of alkenediols, e.g., 3-methylene-1,5-pentanediol (alpha-diol) and 3-methyl-2-pentene-1,5-diol (beta-diol) by reaction of isobutene with formaldehyde. Commonly assigned Ser. No. 491,987 discloses the conversion of alpha-diol to citric acid in an oxidation process. The disclosures of these three applications are incorporated herein by reference, particularly in that they relate to preparation of alpha- and beta-diols, and to conversion of alpha-diol to citric acid.

In view of the present invention, we have also located an article by G. Ohloff in *Chem. Ber.*, Vol. 93, p. 2673 (1960) which discloses the thermal (temperature = 350° C.) splitting off of formaldehyde from a cyclic beta-hydroxy olefin. Also, Smith and Yates in *J. Chem. Soc.* (1965), p. 7242, disclose pyrolysis of but-3-en-1-ol (370° C.) to obtain propene and formaldehyde and the pyrolysis of pent-4-en-2-ol to produce propene and acetaldehyde.

The thermal condensation of formaldehyde with an olefin is disclosed in F. Asinger's book *Monoolefins — Chemistry and Technology*, Pergamon Press (1968), p. 719.

SUMMARY OF THE INVENTION

According to the present invention, a process is provided for producing 3-methyl-3-buten-1-ol from 3-methyl-2-pentene-1,5-diol which comprises heating 3-methyl-2-pentene-1,5-diol at a temperature between 200° and 450° C. in the presence of isobutene.

The conversion of the beta-diol in the process of the present invention can be largely summarized by the following equation:

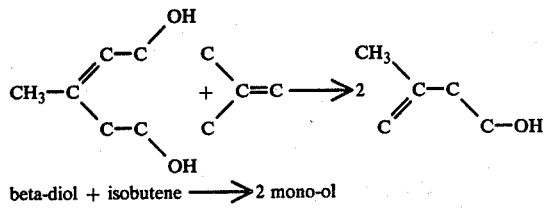

beta-diol + isobutene ⟶ 2 mono-ol

The term "beta-diol" is thus used herein to describe cis and/or trans 3-methyl-2-pentene-1,5-diol, whereas "alpha-diol" is used to describe 3-methylene-1,5-pentanediol, and "mono-ol" is used to describe 3-methyl-3-buten-1-ol.

Among other factors, the present invention is based on our finding that the beta-diol can be converted in good yield to mono-ol and also our conception and finding that the method can be advantageously integrated, as defined hereinbelow, into a synthetic process for producing citric acid.

We have found that a mixture of alpha- and beta-diol can be practically separated by distillation into a beta-diol-rich fraction and an alpha-diol-rich fraction. The alpha-diol can be converted to citric acid by oxidation as described in Ser. No. 491,987. The alpha- and beta-diol mixture can be generated in the first instance by various means, for example from isobutene and formaldehyde, as described in Ser. Nos. 379,511 and 427,176.

According to a preferred embodiment of our invention, a process is provided for improving the yield of citric acid from a citric acid synthesis method wherein citric acid is obtained by: (1) reacting isobutene and/or 3-methyl-3-buten-1-ol, i.e., mono-ol, with formaldehyde to obtain a mixture of 3-methylene-1,5-pentanediol and 3-methyl-2-pentene-1,5-diol, i.e., alpha- and beta-diol; and (2) oxidizing the 3-methylene-1,5-pentanediol to citric acid, which process comprises:

(a) reacting isobutene or 3-methyl-3-buten-1-ol (mono-ol) with formaldehyde to obtain a mixture of 3-methylene-1,5-pentanediol and 3-methyl-2-pentene-1,5-diol (alpha- and beta-diols, respectively);

(b) separating the beta-diol from the alpha/beta-diol mixture, (c) heating the beta-diol to a temperature between 200° and 450° C. in the presence of isobutene to obtain mono-ol;

(d) recycling the mono-ol from step (c) to step (a); and (e) feeding the alpha-diol from step (b) to the oxidation step of the citric acid synthesis method.

Thus, in this preferred embodiment, mono-ol is generated from beta-diol and the thus-obtained mono-ol is reacted with formaldehyde to generate additional alpha-diol. The alpha-diol is advantageously converted to citric acid by oxidation.

Preferred temperature for use in the process of the present invention is between about 200° and 450° C., more preferably between 250° and 440° C.

According to an alternate embodiment, a process is provided for the conversion of beta-diol to a mixture of formaldehyde and 3-methyl-3-buten-1-ol which comprises heating the beta-diol at a temperature in the range 350°–450° C. and without the addition of isobutene being required. According to another alternate, the beta-diol is converted to a mixture of formaldehyde and isobutene by heating the beta-diol at a somewhat higher temperature, for example about 400°–500° C., preferably 450°–500° C. These alternates can be integrated, together with distillation to separate beta-diol from alpha-diol, into a method for synthesizing citric acid, as described above, and wherein the 3-methyl-3-buten-1-ol and formaldehyde and isobutene obtained by the heating are recycled at least in part to the first step of the citric acid synthesis process wherein the alpha- and beta-diol are produced.

Referring again more particularly to the present invention wherein at least one of the steps of the invention embraces the heating of beta-diol in the presence of added isobutene, preferred amounts of added isobutene are between 20% and 80% of the combined beta-diol and isobutene, and more preferably between 50 and 80 weight percent.

Preferably the pressure used in the heating of the beta-diol to obtain the mono-ol is between about 10 and 5000 psig, and more preferably between about 1000 and 3000 psig.

As indicated previously, the present invention preferably embraces a step for separation of beta-diol from alpha-diol by distillation to obtain a beta-diol-rich fraction and an alpha-diol-rich fraction. The term "rich" is used to refer to a fraction containing at least 50 weight percent beta-diol and more preferably at least 80 weight percent beta-diol; and with respect to alpha-diol at least 60 weight percent alpha-diol and more preferably at least 90 weight percent alpha-diol. Some of the constituents which may be present in the respective beta-diol-rich fraction and alpha-diol-rich fraction resulting from the distillation of an alpha/beta-diol mixture, wherein the mixture is generated by reaction of isobutene or mono-ol with formaldehyde, are unidentified by-products from the olefinformaldehyde condensation reaction.

BRIEF DESCRIPTION OF THE DRAWING

The drawing is a schematic process flow diagram illustrating a preferred embodiment of the present invention in simplified form. Isobutene and formaldehyde are fed to diol preparation zone 3 wherein they are reacted to make a mixture of alpha- and beta-diols. The alpha- and beta-diols are fed via line 4 to separation zone 5, which preferably comprises a distillation unit for separating alpha- and beta-diol-rich fractions. The alpha-diol material is fed via line 6 to oxidation zone 7 for oxidation to citric acid, preferably using nitric acid and nitrogen dioxide. After suitable separation, the citric acid is withdrawn via line 8.

Beta-diol is withdrawn from separation zone 5 and is fed as indicated by line 9 to heating zone 10. In heating zone 10 the beta-diol is heated to a temperature between about 250° and 500° C., preferably in the presence of added isobutene introduced via line 11, to obtain mono-ol and/or formaldehyde and isobutene from the beta-diol, and the thus-obtained materials are recycled via line 12 to diol preparation zone 3 for the production of further alpha-diol. The heating zone 10 can include or be integrated with a separation zone so that separated, unconverted, beta-diol from the heating step can be recycled, separated alpha-diol can be fed to zone 7, and separated mono-ol passed via line 12 to diol preparation zone 3.

EXAMPLES

EXAMPLE 1

A 1.1-g portion of beta-diol (containing 14.3% alpha-isomer) was pyrolyzed by passing the diol at an LHSV (liquid hourly space velocity) of 0.55 through an externally heated stainless steel tube having an ID of 3/16" and a length of 8". Carrier nitrogen flow rate was 2-3 cc/min. The temperature was maintained at 390° C. The effluent of 0.87 g was collected in a dry-ice trap. The effluent consisted essentially of only 4 products: alpha- and beta-diols (94%), mono-ol (4%) and formaldehyde (2%). The analyses herein are by weight percent unless indicated otherwise.

EXAMPLE 2

In a manner similar to Example 1, 0.77 g of beta-diol was pyrolyzed at 440° C. and an LHSV of 1.4. The effluent trapped, 0.60 g, consisted of alpha- and beta-diols (83%), mono-ol (9%) and formaldehyde (balance).

EXAMPLE 3

In a manner similar to Example 1, beta-diol (containing 25% alpha-diol), 1.15 g, was pyrolyzed at an LHSV of 1.1 and at 495° C. The effluent trapped (±0.7 g) consisted mainly of isobutene, formaldehyde, small amounts of water and diols (less than 8% of the effluent).

EXAMPLE 4

In a manner similar to Example 1, the beta-diol used in Example 3 (1.44 g) was pyrolyzed at an LHSV of 1.4 and at 475° C. The effluent trapped (±0.9 g) consisted of mainly isobutylene, formaldehyde and a small amount of water.

The above examples 1–4 show that beta-diol can be converted to mono-ol by heating at a temperature between 200°–450° C. Examples 1 and 2 show that at relatively lower temperature little or no isobutene is produced, whereas Examples 3 and 4 show that isobutene is produced from the beta-diol at temperatures between 450° and 500° C.

EXAMPLE 5

A 2-g sample containing 33% 3-methylene-1,5-pentane-diol (alpha-diol) and 55% 3-methyl-2-pentene-1,5-diol (beta-diol) was sealed into a microbomb of approximately 15 ml capacity. The mixture was heated and shaken at 260° C. for 1 hour. A liquid product weighing 1.84 g was obtained which analyzed to be 7.1% alpha-diol, 11.03% beta-diol and 5.74% 3-methyl-3-buten-1-ol (mono-ol). The conversion of diol was 80% and the yield of mono-ol was 10% (by mol).

EXAMPLE 6

A 2-g sample of the same diol mixture was placed in a sealed microbomb with 2 g isobutene. After 1 hour at 260° C., 1.96 g of liquid product was obtained. The product analyzed to be 12.2% alpha-diol, 23.5% beta-diol and 12.7% mono-ol. The diol conversion was 60% and the yield of mono-ol was 32% (by mol).

Thus, Example 6 compared to Example 5 shows increased production of mono-ol from beta-diol when the heating of the beta-diol is carried out in the presence of isobutene, particularly in the presence of isobutene added to the reaction zone.

We claim:

1. A process for improving the yield of citric acid from a citric acid synthesis method wherein citric acid is obtained by (1) reacting isobutene or 3-methyl-3-buten-1-ol with formaldehyde in a reaction zone to obtain a mixture of 3-methylene-1,5-pentanediol and 3-methyl-2-pentene-1,5-diol and (2) oxidizing the 3-methylene-1,5-pentanediol to citric acid, which process comprises:
   (a) reacting isobutene or 3-methyl-3-buten-1-ol (mono-ol) with formaldehyde to obtain a mixture of 3-methylene-1,5-pentanediol and 3-methyl-2-pentene-1,5-diol (alpha- and beta-diols respectively);
   (b) separating the beta-diol from the alpha/beta-diol mixture,
   (c) heating the beta-diol to a temperature between 200° and 450° C. in the presence of isobutene to obtain mono-ol;

(d) recycling the mono-ol from step (c) to step (a); and
(e) feeding the alpha-diol from step (b) to the oxidation step of the citric acid syntehsis method.

2. A process in accordance with claim 1 wherein the amount of isobutene is between 20 and 80 weight percent based on 3-methyl-2-pentene-1,5-diol plus isobutene.

3. A process in accordance with claim 1 wherein the temperature in step (c) is between 250° and 440° C.

* * * * *